United States Patent
Savage et al.

(10) Patent No.: US 7,446,235 B2
(45) Date of Patent: Nov. 4, 2008

(54) METHOD FOR REDUCING MICROCONTAMINANTS DURING SYNTHESIS OF PENTACHLOROPHENOL

(75) Inventors: Phillip E. Savage, Ann Arbor, MI (US); Jianli Yu, Plymouth, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 11/388,816

(22) Filed: Mar. 24, 2006

(65) Prior Publication Data

US 2007/0225529 A1    Sep. 27, 2007

(51) Int. Cl.
*C07C 39/00* (2006.01)
*C07C 37/68* (2006.01)

(52) U.S. Cl. .................... 568/776; 568/755

(58) Field of Classification Search ............... 568/755, 568/776
See application file for complete search history.

(56) References Cited

U.S. PATENT DOCUMENTS

| 4,280,012 | A | * | 7/1981 | Pastura et al. ............ 568/755 |
| 4,294,996 | A | | 10/1981 | Wetzel et al. |
| 4,358,402 | A | * | 11/1982 | Padget ....................... 525/192 |
| 4,376,220 | A | | 3/1983 | Wetzel et al. |
| 4,400,556 | A | | 8/1983 | Wetzel et al. |
| 4,766,103 | A | | 8/1988 | Cobb |
| 5,026,926 | A | | 6/1991 | Leblanc et al. |
| 5,476,975 | A | | 12/1995 | Ruddick et al. |
| 5,698,829 | A | | 12/1997 | Ruddick et al. |
| 2003/0166988 | A1 | | 9/2003 | Hazen et al. |

OTHER PUBLICATIONS

Buser et al., Det.of Polychlorinated dibenzo-p-dioxins & dibenzofurans in comm. pentachlorophenols by combined gas chrom.-mass spect.,J of the AOAC, vol. 59,No. 3, 1976,pp. 562-569.
Yu et al., Reaction Pathways in Pentachlorophenol Synthesis, 1. Temperature-Programmed Reaction, Ind. Eng. Chem. Res. 2004, 43, pp. 5021-5026.
Yu et al., Reaction Pathways in Pentachlorophenol Synthesis, 2. Isothermal Reaction, Ind. Eng. Chem. Res., 2004, 43, pp. 6292-6298.
Muller et al., Chlorophenols. in Ullmann's Encyclopedia of Industrial Chemistry (on-line edition) DOI 10.1002/14356007/a07_001, Posted Jun. 15, 2000.
International Search Report for S.N. PCT/US07/64752 dated Mar. 13, 2008 (4 pages).

* cited by examiner

*Primary Examiner*—Shaojia Anna Jiang
*Assistant Examiner*—Jennifer Y Cho
(74) *Attorney, Agent, or Firm*—Dierker & Associates, P.C.

(57) ABSTRACT

A method for reducing contaminants during synthesis of pentachlorophenol includes providing a phenol-based starting material and a catalyst, which form a reaction mixture. A chlorine flow is introduced so that it is in contact with the reaction mixture, and the starting material and chlorine are reacted via a temperature-programmed reaction. The chlorine flow is terminated at a predetermined temperature prior to an end of the temperature-programmed reaction and/or at a point where the yield of pentachlorophenol is less than about 95%.

27 Claims, 9 Drawing Sheets

METHOD FOR REDUCING MICROCONTAMINANTS DURING SYNTHESIS OF PENTACHLOROPHENOL

BACKGROUND

The present disclosure relates generally to synthesis of pentachlorophenol, and more particularly to method(s) for reducing microcontaminants during synthesis of pentachlorophenol.

Pentachlorophenol is a wood preservative generally manufactured via catalyzed chlorination of phenol or chlorophenol mixtures in the liquid phase. The process for synthesizing pentachlorophenol often results in the production of ppm levels of polychlorinated dibenzodioxins (PCDD) and polychlorinated dibenzofurans (PCDF) with six or more chlorine substituents.

Generally, such processes have a large increase in the toxic equivalent (TEQ) concentration during a narrow window in time near the maximum pentachlorophenol yield. Further, the TEQ concentration seems to increase further in the cooled and solidified post-reaction samples.

Reduction of the microcontaminant levels in the pentachlorophenol product is desirable for many reasons, and in particular, for environmental purposes. The toxins that may be produced during synthesis of the pentachlorophenol product may cause or increase the risk of undesirable environmental and health effects.

As such, it would be desirable to provide a method for synthesizing pentachlorophenol with substantially reduced amounts of microcontaminants.

SUMMARY

A method for reducing contaminants during synthesis of pentachlorophenol includes providing a phenol-based starting material and a catalyst. The phenol-based starting material and catalyst form a reaction mixture. A chlorine flow is introduced so that it is in contact with the reaction mixture, and the starting material and chlorine are reacted via a temperature-programmed reaction. The chlorine flow is terminated at a predetermined temperature prior to an end of the temperature-programmed reaction and/or at a point where the yield of pentachlorophenol is less than about 95%.

BRIEF DESCRIPTION OF THE DRAWINGS

Features and advantages of the present disclosure will become apparent by reference to the following detailed description and drawings. In each of the Figures, the TEQ level is given in ppm for selected points on each plot.

DETAILED DESCRIPTION

Embodiments of the method disclosed herein advantageously reduce the formation of toxic equivalent (TEQ) concentrations of PCDD and PCDF during synthesis of pentachlorophenol. Without being bound to any theory, it is believed that such a reduction may reduce the health and/or environmental risks generally associated with pentacholophenol.

An embodiment of the method includes reacting a phenol-based starting material and a catalyst to form a reaction mixture. The reaction mixture may be contacted with chlorine in a reactor so as to form pentachlorophenol via a temperature-programmed reaction. As referred to herein, the term "temperature-programmed reaction" means that the temperature of the reaction mixture is controlled according to a predetermined course in which it varies over time. In other embodiments, the temperature of the reactor is gradually increased throughout the temperature-programmed reaction. The reaction generally begins at the melting point of the starting material, and the reactor temperature generally does not exceed 190° C.

As the reaction progresses, the reaction mixture may be substantially continuously mixed. Stirring and other mixing techniques are well known to those skilled in the art, and commercial mixers are readily available.

Non-limitative examples of suitable phenol-based starting materials include phenols, chlorophenols (a non-limitative example of which includes 2,4,6-trichlorophenol), and/or combinations thereof. It is to be understood that any suitable amount of starting material may be used. Furthermore, the amount of starting material may depend on, at least in part, the scale of the reaction.

Catalysts that are effective for catalyzing the chlorination of phenols are generally known in the art, and it is to be understood that any suitable catalyst may be selected for use in embodiment(s) of the method disclosed herein. In an embodiment, the catalyst is $AlCl_3$. Generally, the amount of the catalyst ranges from about 0.25 wt. % to about 1.5 wt. %. The amount of catalyst may vary depending, at least in part, on the scale of the reaction.

A chlorine flow/feed is initiated so that it contacts the reaction mixture at a predetermined time and/or at a predetermined temperature. In certain embodiments, the chlorine flow is initiated when the reactor temperature reaches about 105° C. In other embodiments, the chlorine flow is initiated as soon as the reaction mixture melts. The chlorine flow/feed may be introduced at any suitable flow rate.

The freezing point/melting point of the reaction mixture increases as chlorination proceeds; for this reason, the reactor temperature is gradually increased as the reaction progresses, so as to substantially maintain a liquid phase of the reaction mixture (i.e., above the melting point). In preferred embodiments, the temperature is maintained at less than about 5 degrees, more preferably less than about 2 degrees, and still more preferably less than about 0.5 degrees above the melting point of the reaction mixture.

As the synthesis of pentachlorophenol progresses, other chlorinated phenols may form, and then be converted or consumed, or remain in the final product. Examples of other chlorinated phenols that may form during the synthesis of pentachlorophenol include 2-chlorophenol, 4-chlorophenol, 2,4-chlorophenol, 2,6-di-chlorophenol, 2,4,6-tri-chlorophenol, and/or tetrachlorophenol.

Embodiments of the method include terminating the chlorine flow at a predetermined temperature prior to an end of the temperature-programmed reaction. It has been discovered that terminating the chlorine flow prior to the end of the synthesis substantially reduces TEQ concentrations in both the pentachlorophenol product from the reactor and the post-reaction pentachlorophenol product. It has also been discovered that TEQ concentrations are further reduced when some tetrachlorophenol remains unconverted.

Thus, according to preferred embodiments, the chlorination flow is terminated when the reaction mixtures reaches a temperature ranging from about 170° C. to about 190° C. In specific non-limitative examples, the chlorine flow is terminated at 174° C., 177° C., 180° C., 183° C. or 186° C. By way of example only, where the phenol-based starting material is 2,4,6-trichlorophenol and the chlorine flow is terminated at a temperature between about 170° C. to about 190° C., the toxic equivalent concentration of microcontaminants in a post-reaction sample of pentachlorophenol is less than about 0.85 ppm. By way of further example, where the phenol-based starting material is phenol and the chlorine flow is terminated at a temperature between about 170° C. to about 190° C., the toxic equivalent concentration of microcontaminants in a post-reaction sample of pentachlorophenol is less than about 2.4 ppm.

Prior to termination, the chlorine flow may be gradually reduced as the temperature is raised. The initial/first chlorine flow rate may be reduced to a second flow rate after a first predetermined time lapses or a first predetermined temperature is reached, and then the second flow rate may be reduced to a third flow rate after a second predetermined time lapses or a second predetermined temperature is reached. It is to be understood that the flow rate may be reduced continuously or as many times as desirable prior to termination of the flow. Furthermore, the time(s) at which the flow rate is reduced may be at any suitable time(s), depending, at least in part, on the progression of the synthesis.

In other embodiments, the chlorine flow is terminated at a point where the yield of pentachlorophenol (based on the amount of starting material) is less than about 95%. By way of example, the chlorine flow may be terminated at a point where the pentachlorophenol yield is less than about 80%, or less than about 85%. In an alternate embodiment, the chlorine flow may be terminated at a point where the tetrachlorophenol yield remains greater than about 1%, more preferably between about 1% and about 15%, and still more preferably between about 2% and about 10%.

The method may also include adding a metal to the reaction mixture prior to terminating the chlorine flow. Without being bound to any theory, it is believed that the addition of the metal may further reduce the TEQ concentration of microcontaminants in the pentacholorphenol. Non-limitative examples of the metal include nickel, cobalt, manganese, and combinations thereof. Generally, the metal may be in any suitable form, including powder form.

The metal may be introduced in an amount so that its concentration in the reaction mixture is from about 100 ppm to about 5,000 ppm. Alternately, the metal may be introduced in an amount so that its concentration in the reaction mixture is from about 800 ppm to about 5,000 ppm. Some specific non-limitative examples of the amount of metal added include 833 ppm, 1,250 ppm, and 2,500 ppm.

The metal may be added to the reaction mixture prior to initiating the chlorine flow (e.g., when reactor temperature is about 90° C.), or prior to terminating the chlorine flow (e.g., when the reactor temperature is about 160° C.). It is believed that adding the metal when or after the chlorine flow is terminated is generally not as effective in inhibiting the formation of TEQ concentrations.

In a non-limitative example in which the phenol-based starting material is 2,4,6-trichlorophenol, the chlorine flow rate is stopped at a temperature of about 180° C., and nickel is added prior to chlorine flow termination, the toxic equivalent concentration of contaminants in a post-reaction sample of pentachlorophenol is less than about 0.5 ppm. In an alternate non-limitative example in which the phenol-based starting material is phenol, the chlorine flow rate is stopped at a temperature of about 180° C., and nickel is added prior to chlorine flow termination, the toxic equivalent concentration of contaminants in a post-reaction sample of pentachlorophenol is generally not greater than about 1.1 ppm.

In certain embodiments, upon termination of the chlorine flow, an inert gas flow may be introduced into the reaction mixture. A non-limitative example of such an inert gas is nitrogen gas ($N_2$). It is to be understood that the inert gas flow may also be used in embodiments of the method with or without the addition of metal.

In any of the embodiments of the method disclosed herein, additional catalyst material or tetrachlorophenol may be added after the chlorine flow is terminated. While the experimental details below indicate that such an addition may have no appreciable effect on the TEQ concentrations, it is believed that an aluminum chloride catalyst may accelerate consumption of any residual chlorine, and/or that tetrachlorophenol may provide additional material with which the residual chloride may react, thereby reducing the formation of contaminants.

In still other embodiments of the method, the temperature ramp may be terminated at the same time that the chlorine flow is terminated, and/or chlorine sponges may be added to the reaction mixture after termination of the chlorine flow. Without being bound to any theory, it is believed that altering the method by incorporating different combinations of the previously described steps may further reduce the TEQ concentrations during the synthesis of pentachlorophenol when the chlorine flow rate is terminated prior to the end of the temperature-programmed reaction.

To further illustrate embodiment(s) of the present disclosure, various examples are given herein. It is to be understood that these examples are provided for illustrative purposes and are not to be construed as limiting the scope of the disclosed embodiment(s).

EXAMPLES

The following experiments were performed in a laboratory. As such, the specifics (i.e., quantities, stir rates, flow rates, etc.) apply to a lab-scale synthesis. It is to be understood that quantities, stir rates, flow rates, etc. will be larger when synthesis is performed on a commercial scale.

Experimental Details—Chlorine Flow Rate Termination

For most of the following experiments, chlorine gas was bubbled continuously through a liquid phase containing, initially, about 300 g of molten 2,4,6-trichlorophenol and about 0.75 g $AlCl_3$ catalyst. The pentachlorophenol synthesis was performed via a temperature-programmed reaction. The reactor temperature was gradually increased from about 105° C., the temperature at which the chlorine flow/feed was initiated, to at greatest 190° C. during the synthesis to keep the contents in the liquid phase at all times. The freezing point/melting point of the mixture increases as chlorination proceeds, so the reactor temperature was increased to remain just above the freezing point.

Samples were withdrawn periodically by inserting a glass rod into the reactor. The liquid on the rod quickly solidified when removed from the reactor and cooled to room temperature. At the end of each synthesis, the reactor contents were poured into disposable aluminum pans to cool. Samples of the post-reaction solid products may also be collected and analyzed.

The samples were analyzed by capillary column GC to determine the amounts of tri-, tetra-, and pentachlorophenol. The microcontaminant levels were determined by an aryl hydrocarbon receptor capture (AhRC) method that uses real-time polymerase chain reaction (PCR) for quantification. This AhRC PCR bioassay provides the TEQ concentration of PCDDs and PCDFs in each sample.

Base Case

All samples were analyzed from a base-case synthesis experiment. The results from later experiments may be compared with the results of the base-case.

In the base-case synthesis, about 0.25 wt. % (about 0.75 g) $AlCl_3$ catalyst was added to molten trichlorophenol at 90° C. Chlorine flow was introduced at a rate of about 1.5 mol/hr, which was reduced to about 1.1 mol/hr after about 2.5 hours, and was further reduced to about 0.9 mol/hour after a 30 minute temperature ramp. The stirring rate was set at about 100-120 rpm.

Figure 1:
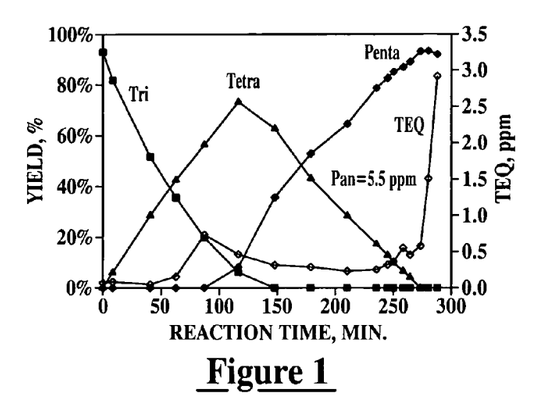
FIG. 1 is a graph depicting the temporal variation of chlorophenol yields and toxic equivalent (TEQ) concentrations for synthesis in which chlorine flow was reduced throughout the process.

FIG. 1 shows that the TEQ concentration is low initially, but increases as tetrachlorophenol forms. As depicted, the TEQ concentration is less than about 0.5 ppm as long as tetrachlorophenol is still present in the sample. After the tetrachlorophenol is consumed, however, the TEQ concentration increases rapidly from about 0.56 to about 2.9 ppm. The TEQ concentration continues to increase, to about 5.5 ppm, in the post-reaction sample (the TEQ concentration for the post-reaction sample taken from the aluminum pans is referred to as "Pan" in applicable Figures).

These observations suggest that product with TEQ concentrations around 0.5 ppm may be obtained by stopping the synthesis while some tetrachlorophenol remains in the sample.

Termination of Chlorine Flow

Figure 2A:
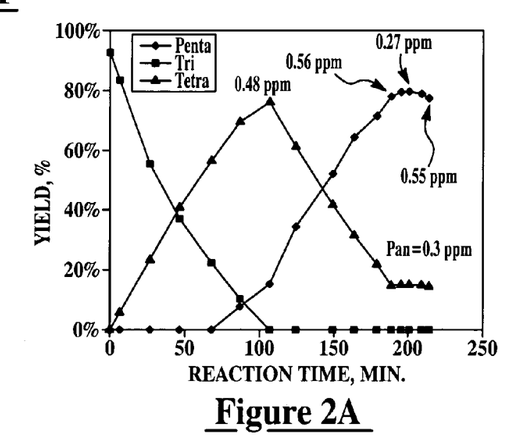
FIGS. 2A-2B are graphs depicting the temporal variation of chlorophenol yields and TEQ concentrations for synthesis with chlorine flow stopped, respectively, at 174° C. and 186° C.

FIG. 2A depicts results from experiments where the chlorine flow was stopped at 189 minutes and where the reaction mixture had reached 174° C. The maximum pentachlorophenol yield, as shown in FIG. 2A, was about 80% at 201 minutes, with about 0.27 ppm TEQ concentration. The post-reaction sample had a pentachlorophenol yield of about 77% with about 0.3 ppm TEQ concentration. The final product contained about 15% tetrachlorophenol.

Figure 2B:
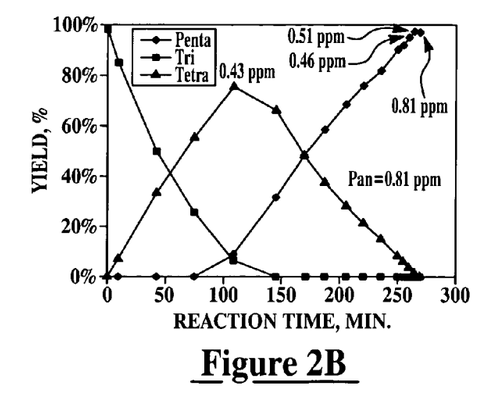

FIG. 2B depicts results from experiments where the chlorine flow was stopped at 266 minutes and where the reactor temperature was 186° C. When comparing FIGS. 2A and 2B, the maximum pentachlorophenol yield and the TEQ concentration were higher in the sample of FIG. 2B than in the sample of FIG. 2A. FIG. 2B shows that the pentachlorophenol yield was about 97% and the TEQ concentration was about 0.51 ppm when the chlorine flow was terminated. The TEQ concentration increased to about 0.81 ppm after about 5 additional minutes of reaction time. The post-reaction sample had a pentachlorophenol yield of about 97% with a 0.81 ppm TEQ concentration. The final product contained no residual tetrachlorophenol, as this intermediate product had been consumed completely. It is apparent that the TEQ concentrations are lower in FIG. 2A, where some tetrachlorophenol remains unconverted, than in FIG. 2B, where it had all been consumed. Thus, the precise temperature at which the chlorine flow is terminated may alter the TEQ concentration.

In comparing both FIGS. 2A and 2B to FIG. 1, the TEQ concentrations in the post-reaction samples of FIGS. 2A and 2B were lower than those from the base-case synthesis run (FIG. 1). Without being bound to any theory, it is believed that stopping the chlorine flow near, but prior to, the end of the synthesis run is an effective way to stop the formation of higher TEQ concentrations. Still further, the results of FIGS. 2A and 2B indicate that increases in TEQ concentration that occur post-reaction (as the molten pentachlorophenol cools) may be substantially inhibited by stopping the chlorine flow in the reactor prior to the end of the run.

Addition of $AlCl_3$ or Tetrachlorophenol

Figure 3A:
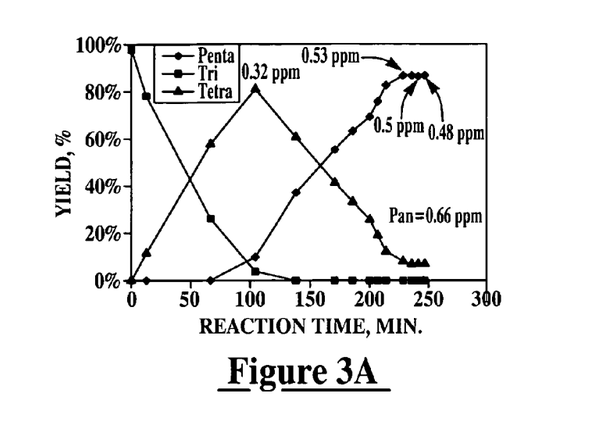
FIG. 3A is a graph depicting temporal variation of chlorophenol yields and TEQ concentrations for synthesis with chlorine flow stopped at 180° C., and the addition of 0.75 g $AlCl_3$.
Figure 3B:
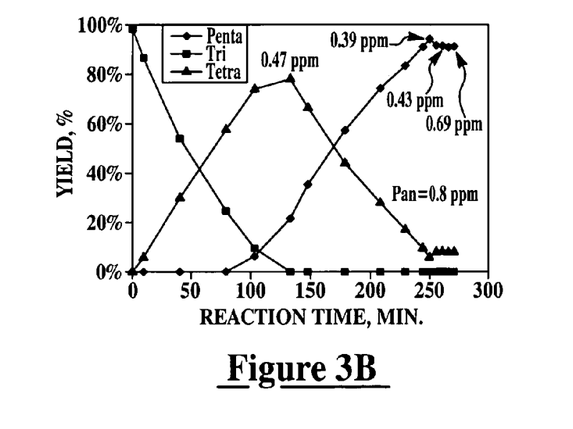
FIG. 3B is a graph depicting temporal variation of chlorophenol yields and TEQ concentrations for synthesis with chlorine flow stopped at 180° C., and the addition of 10 g tetrachlorophenol.

FIGS. 3A and 3B illustrate data from synthesis experiments where the chlorine flow was stopped at 180° C., and at the same time about 0.75 g of $AlCl_3$ catalyst (FIG. 3A) or 10 g of tetrachlorophenol (FIG. 3B) was added.

In FIG. 3A, with added $AlCl_3$, the post-reaction sample (pan) had a pentachlorophenol yield of about 87% with about 0.66 ppm TEQ concentration. In FIG. 3B, with added tetrachlorophenol, the post-reaction sample (pan) had about 91% pentachlorophenol with about 0.8 ppm TEQ concentration. In both examples, the residual tetrachlorophenol yield was about 6% when the chlorine flow stopped.

The results shown in both FIGS. 3A and 3B indicate that the TEQ concentrations are no lower than those in FIGS. 2A and 2B at equivalent points during the reactions. As such, it is believed that neither the addition of $AlCl_3$ nor of tetrachlorophenol near the end of the synthesis results in a substantial reduction or a substantial increase in the concentration of microcontaminants.

FIGS. 2A, 2B, 3A and 3B show that the TEQ concentrations at the maximum tetrachlorophenol yields were typically lower than those of the final pentachlorophenol sample in the aluminum pan. On average, about two-thirds of the final TEQ value has developed by the time the maximum tetrachlorophenol yield is attained.

Purging with Nitrogen and Stopping Temperature Program

The previously described syntheses of pentachlorophenol likely have residual chlorine present at the end of the reactions. As the potential exists for the residual chlorine to affect the TEQ concentrations in subsequent samples, this experiment focused on removing as much of the residual chlorine as possible. This was accomplished by bubbling an inert gas ($N_2$) through the reaction mixture after stopping the chlorine flow.

The effect of inert gas introduction was tested by performing three more syntheses and stopping the chlorine flow at different temperatures near the end of the run (177° C. (FIG. 4A), 180° C. (FIG. 4B) and 183° C. (FIG. 4C)). 0.25 wt. % catalyst and a catalyst addition procedure (added at 90° C.) were used for these experiments.

Figure 4A:
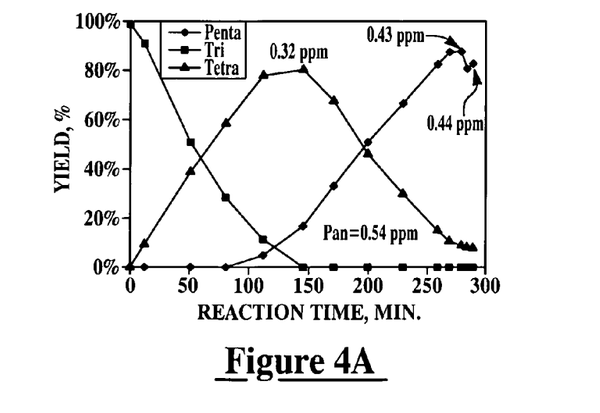
FIGS. 4A-4C are graphs depicting temporal variation of chlorophenol yields and TEQ concentrations for synthesis with chlorine flow stopped, respectively, at 177° C., 180° C., and 183° C., followed by nitrogen purging.
Figure 4B:
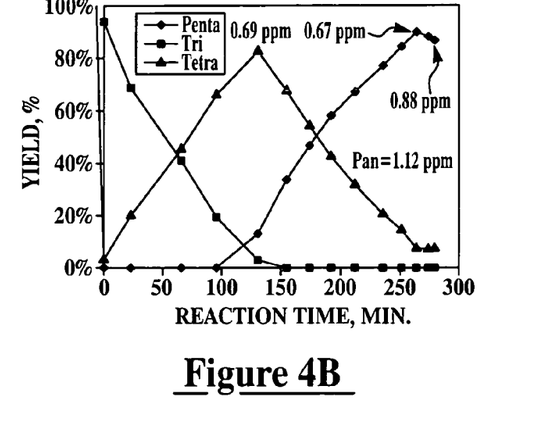
Figure 4C:
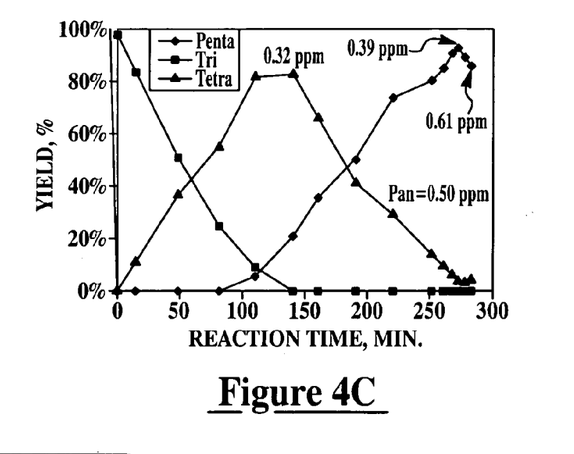

The results in FIGS. 4A, 4B and 4C are similar to those obtained from analogous experiments that terminated chlorine flow at slightly different temperatures and without a nitrogen purge (see FIG. 2). In FIGS. 4A-4C, the TEQ concentration near the end of the run was about 0.65±0.2 ppm, and it was occasionally more than 50% higher than the TEQ value that had been reached at the maximum tetrachlorophenol yield. These results suggest that purging with nitrogen provides little additional benefit in terms of reducing the TEQ concentration in the post-reaction product. Without being bound to any theory, however, it is believed that such purging may be beneficial at a commercial scale (i.e., where volumes are larger and the gas-liquid surface area/reactor volume is smaller).

It is noted that FIG. 4B illustrates TEQ concentrations higher than any of the TEQ concentrations in FIGS. 4A and 4C. As all the values in FIG. 4B are high and inconsistent with the results of FIGS. 4A and 4C, it is believed that the results are spurious and may not indicate a genuine difference with the other experiments.

Figure 5:
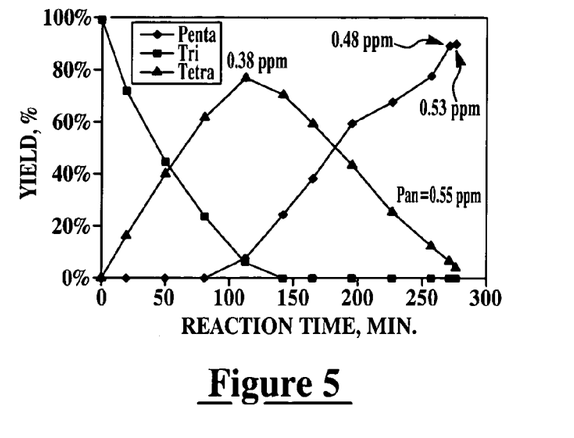
FIG. 5 is a graph depicting temporal variation of chlorophenol yields and TEQ concentrations for synthesis with chlorine flow and temperature ramp stopped at 183° C., followed by nitrogen purging.

In the experiments involving nitrogen purging, the reactor temperature continued to increase to the same final value (188° C.) even after the chlorine flow was stopped at some predetermined lower temperature. Another experiment was run to determine whether the continued temperature ramp had any effect on the TEQ concentration. In this experiment, a reaction was run where both the temperature ramp and chlorine flow were stopped together at 183° C. FIG. 5 illustrates the results from this experiment. When FIG. 4C is compared to FIG. 5, it is evident that neither the TEQ concentration nor the pentachlorophenol yield were substantially altered by stopping the temperature ramp.

Adding Phenol with Nitrogen Purge

Figure 6A:
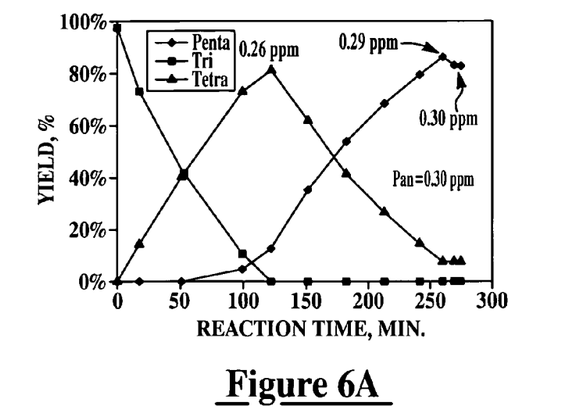
FIGS. 6A-6B are graphs depicting temporal variation of chlorophenol yields and TEQ concentrations for synthesis with chlorine flow stopped respectively at 180° C. and 183° C., followed by nitrogen purging and the addition of phenol.
Figure 6B:
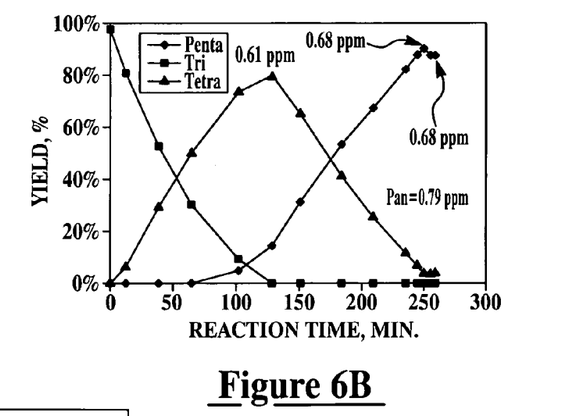

Another method for potentially ridding the reaction mixture of any residual chlorine is to add phenol to serve as a "chlorine sponge" at the reaction stopping point. FIGS. 6A and 6B depict the results of two synthesis experiments where about 10 g of phenol were added at different chlorine flow stopping points (180° C. and 183° C., respectively). The results may be compared with the results in FIGS. 4A-4C. The experiments were identical except for the addition of phenol at the time when chlorine flow stopped.

Comparing FIGS. 6A and 4B, the conclusion may be drawn that the addition of phenol at 180° C. reduces the TEQ concentration by about a factor of three to four. This effect may not be real, however, because the TEQ concentrations in FIG. 4B may be too high, as discussed earlier. A comparison of FIGS. 6B and 4C shows that the TEQ concentrations are higher in the run with added phenol. It is to be understood that this difference is small, and within the experimental uncertainty. It appears that the addition of phenol at 183° C. had no appreciable effect on the TEQ concentration. The lack of an effect at 183° C. also supports the notion that the TEQ concentrations in FIG. 4B are high. Given these results, the addition of phenol to the reaction mixture near the end of the run does not substantially change the TEQ concentration.

Figure 7:
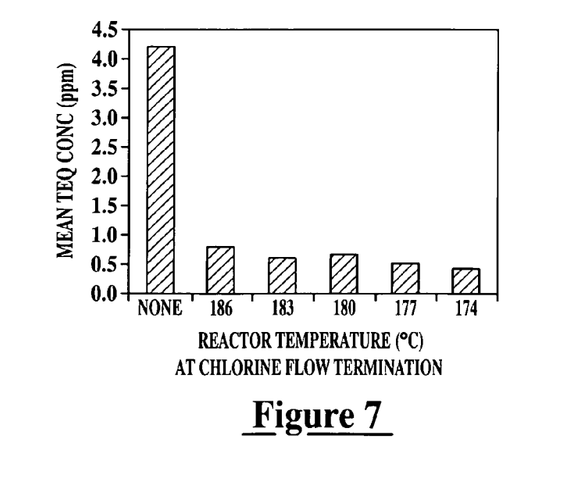
FIG. 7 is a graph depicting the average end-of-run TEQ concentrations from experiments with different chlorine flow stopping temperatures.

FIG. 7 illustrates the TEQ concentrations obtained by stopping the chlorine flow rate before the end of the synthesis experiment. Specifically, FIG. 7 shows the average of the TEQ concentrations in the final reactor sample and the post-reaction sample for the base-case experiment and for experiments with chlorine flow stopped at different temperatures. All of the previously discussed data for each specific chlorine flow stopping temperature were averaged to compute the TEQ concentrations shown in FIG. 7. For example, the data in FIGS. 3, 4B, and 6A were used to calculate the mean TEQ concentration for stopping chlorine flow at 180° C. Implicit in this calculation, then, is the notion that the addition of "chlorine sponges", purging with $N_2$, and stopping the temperature ramp all had much less influence on TEQ concentration than did stopping the chlorine flow rate.

The data of FIG. 7 shows that terminating the chlorine flow rate at 186° C. substantially prevents the formation of microcontaminants that otherwise may have been present in the product. The TEQ concentration appears to decrease further as the temperature at which chlorine flow is stopped is reduced. It is to be understood that the composition of the final product at the different temperatures is different than the one produced in the base-case in that it contains increasing amounts of tetrachlorophenol.

Synthesis Starting with Phenol

Pentachlorophenol was synthesized with phenol as the starting material to determine whether using a starting material other than 2,4,6-trichlorophenol produced any differences in the results.

About 143 g of phenol (an amount that should lead to an equivalent amount of pentachlorophenol product, by moles, obtained when about 300 g of 2,4,6-trichlorophenol is used) were added to a reactor at 60° C. with 0.75 g of $AlCl_3$ (about 0.25 wt. % based on trichlorophenol). The same stirring rate (100-120 RPM) and chlorine flow rate (1.5 mol/hr) as experiments that started with trichlorophenol were used.

The temperature in the reactor increased quickly to above 100° C. after the chlorine flow began, because of the exothermic reaction. Samples were collected about every 30 minutes. The reaction required more than 10 hours to reach the desired end point. The chlorine flow rate and temperature ramp were stopped at 180° C., so that some tetrachlorophenol was left in the final product.

The chlorinated phenols that formed were 2-, and 4-chlorophenol, 2,4- and 2,6-di-, 2,4,6-tri-, tetra-, and pentachlorophenol. The yields of the chlorinated phenols were analyzed by gas chromatography with thermal conductivity detection. The chlorophenol yields, TEQ concentrations for selected samples, and the reactor temperature profile (illustrated by the Δ plot line) appear in FIG. 8. The yields of the two mono- and two dichlorophenols were summed in the plot. The mono-, di-, and trichlorophenol yields increased to maximum values of about 84% at 60 minutes, about 83% at 151 minutes and about 92% at 241 minutes, respectively, and then decreased to zero at the time the next product reached its maximum yield (i.e., the yield of monochlorophenol was zero at the time the dichlorophenol yields reached a maximum). The yield of tetrachlorophenol increased to its maximum value of about 74% at 464 minutes. The amount of tetrachlorophenol remaining at the end of the run was about 8%, and the pentachlorophenol yield was about 83% in this sample.

Figure 8:
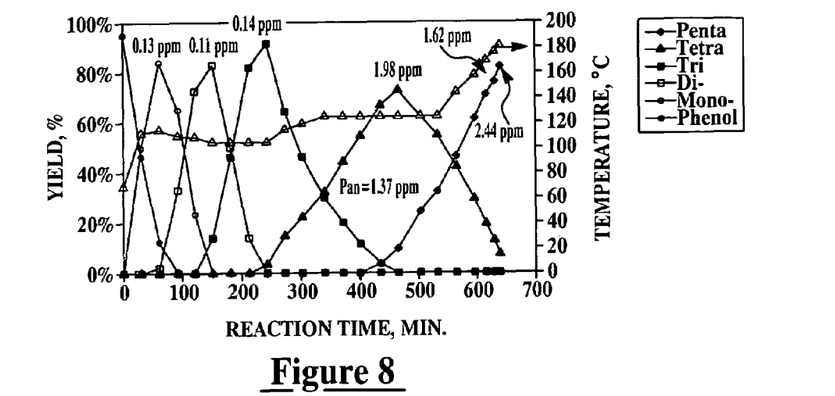
FIG. 8 is a graph depicting temporal variation of chlorophenol yields and TEQ concentrations for synthesis starting with phenol, and with chlorine flow and temperature ramp stopped at 180° C., followed by nitrogen purging.

The TEQ concentrations were about 0.13, about 0.11, and about 0.14 ppm at the points of the maximum mono-, di-, and trichlorophenol yields. These concentrations should be considered estimates because the bioassay used was calibrated with pentachlorophenol samples. A different chemical matrix existed in these samples with the less chlorinated phenols. Nevertheless, the results indicate that the TEQ values were very low until tetrachlorophenol was formed. The TEQ concentration increased to about 1.98 ppm at the maximum tetrachlorophenol yield, and it was about 1.62, about 2.44, and about 1.37 ppm in the last two pentachlorophenol samples taken from the reactor and the pentachlorophenol sample in the aluminum pan, respectively. The TEQ concentration did not change appreciably after the maximum tetrachlorophenol yield appeared. Rather, it was consistently about 1.9±0.5 ppm.

This TEQ concentration of about 2 ppm is higher that those obtained from syntheses starting with trichlorophenol. However, these results are still less than the 5.5 ppm in the pan sample of FIG. 1. The higher TEQ concentration may be a result of the experiment with phenol lasting about 200 minutes longer to go from tri- to pentachlorophenol than did the runs started with trichlorophenol. The longer reaction time may have provided greater opportunity for the formation of microcontaminants.

Experimental Details—Chlorine Flow Rate Termination and Addition of Metal

For the following experiments, pentachlorophenol was formed by the $AlCl_3$-catalyzed (0.25 wt. %) chlorination of trichlorophenol in a round bottom flask. Chlorine gas continuously bubbled through the molten reaction medium. As chlorination occurred, the melting point of the mixture increased, so the reactor temperature was increased to keep it a few degrees above the melting point. Samples of the reaction mixture were withdrawn periodically and analyzed for chlorophenols (by gas chromatography) and for microcontaminants (by bioassay). At the end of the experiments, the reactor contents are poured into a disposable aluminum pan to cool and solidify. This post-reaction product was often analyzed. Acetone, aqueous $HNO_3$ solution, and methanol were used successively to clean the reactor after each experiment.

The chlorine flow in all of the experiments was terminated when the reactor temperature reached 180° C. This operation mode leaves a small amount of tetrachlorophenol unconverted in the reactor.

Varying Time of Nickel Addition

Three experiments were performed in which the time at which nickel powder (about 0.75 g≈2500 ppm) was added was the variable. In all cases, the chlorine flow to the reactor was replaced with $N_2$ when the reactor temperature reached 180° C.

Figure 9A:
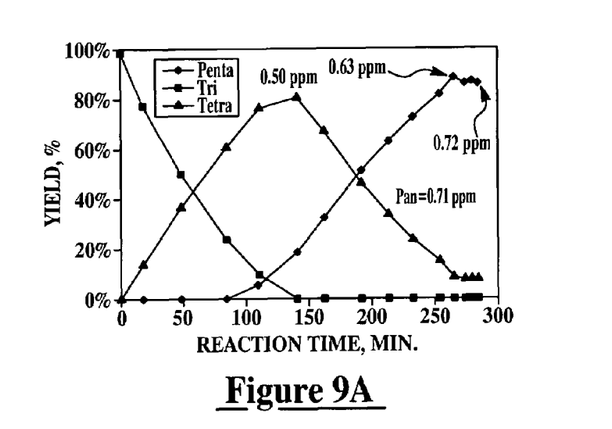
FIGS. 9A-9C are graphs depicting temporal variation of chlorophenol yields and TEQ concentrations for synthesis with chlorine flow stopped at 180° C., and with 2500 ppm of nickel added at 180° C., 160° C., and 90° C., respectively.

The results shown in FIGS. 9A may be compared with the other experiments terminating chlorine flow at 180° C. The conditions of the experiments are similar except for the addition of Ni powder at 180° C. Results from seven different experiments that stopped chlorine flow at 180±3° C. were used to calculate mean TEQ concentrations of 0.38±0.12 ppm for the sample at the maximum tetrachlorophenol yield, 0.53±0.14 ppm for the last sample taken from the reactor, and 0.59±0.18 ppm for the post-reaction sample from the aluminum pan. The uncertainties shown here are the standard deviations about the mean.

The TEQ concentrations in FIG. 9A are slightly higher than the means given above, but they are within the range of TEQ values seen experimentally from experiments with chlorine flow stopping at about 180° C. without added Ni. As such, the addition of Ni near the end of the run does not appear to have an effect on the TEQ concentrations.

Figure 9B:
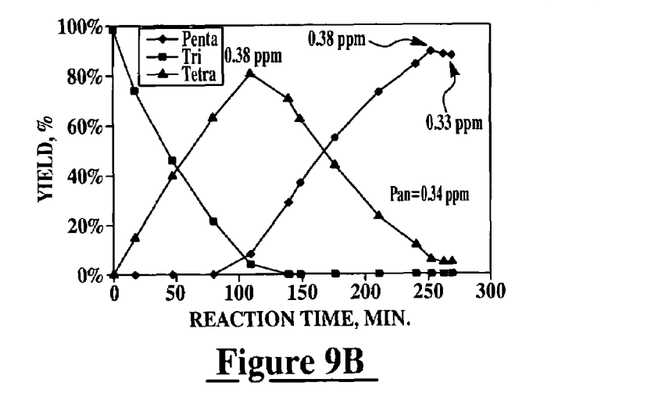
Figure 9C:
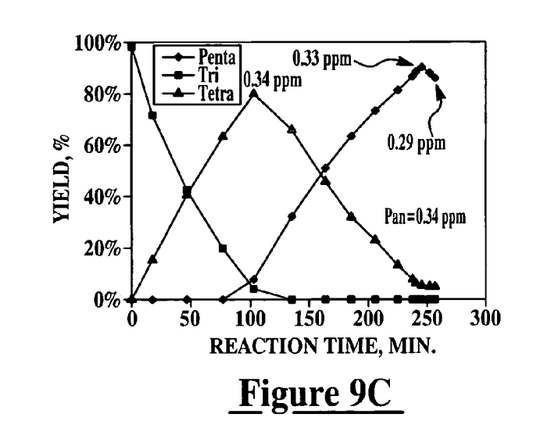

The results shown in FIGS. 9B and 9C indicate that adding Ni earlier in the synthesis does seem to have benefits. In FIG. 9B, the Ni was added when the reactor reached about 160° C., and in FIG. 9C, the Ni was added (along with the catalyst) at 90° C. In both cases, the TEQ concentrations were around 0.3 ppm in all samples, and there was no increase in TEQ concentration after the maximum tetrachlorophenol yield was reached.

Collectively these results suggest that Ni powder does not substantially alter the TEQ concentration present at the maximum tetrachlorophenol yield, and that it does not substantially reduce the TEQ concentration much when added near the end of the run. Rather, the results indicate that nickel inhibits the TEQ concentration increase that had occurred in other runs between the maximum tetrachlorophenol yield and the final pentachlorophenol product.

Figure 10A:
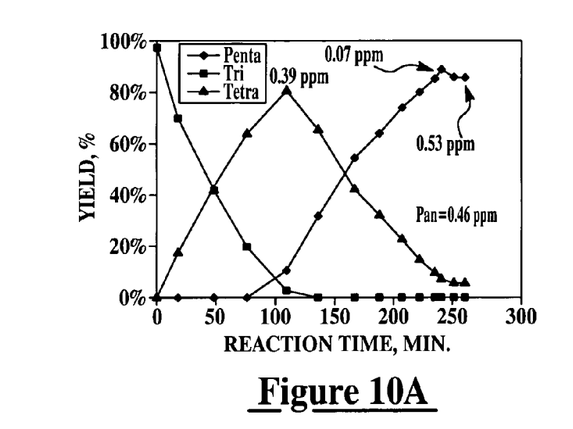
FIGS. 10A and 10B are graphs depicting temporal variation of chlorophenol yields and TEQ concentrations for synthesis with chlorine flow stopped at 180° C., and 2500 ppm nickel added at 90° C.
Figure 10B:
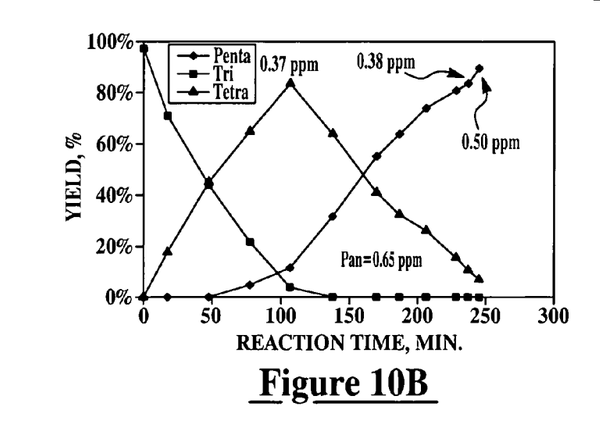
Figure 10C:
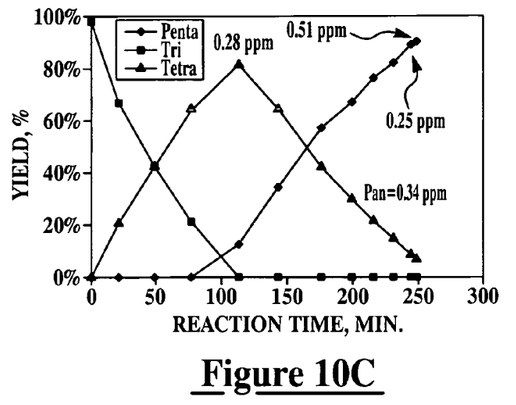
FIG. 10C is a graph depicting temporal variation of chlorophenol yields and TEQ concentrations for synthesis with chlorine flow and temperature ramp stopped at 180° C., and 2500 ppm nickel added at 90° C.

Three additional experiments were performed to check the reproducibility of these results. FIGS. 10A and 10B show the chlorophenol yields and TEQ concentrations obtained at the same experimental conditions used to generate FIG. 9C. The TEQ values were about 0.38 ppm at the maximum tetrachlorophenol yield, and about 0.5 ppm for the last sample withdrawn from the reactor. The TEQ concentrations for the post-reaction pentachlorophenol samples taken from the aluminum pan were about 0.46 ppm and about 0.65 ppm. FIG. 10C illustrates the results from an experiment where the chlorine flow and the temperature ramp were stopped at 180° C. The TEQ concentration was about 0.25 ppm for the last sample from the reactor, and about 0.34 ppm for the post-reaction pentachlorophenol product. These TEQ concentrations are similar to those shown in FIG. 9C, and thus confirm that the TEQ reductions obtained by adding Ni at the start of the synthesis reaction are reproducible.

The accuracy of the cleaning procedure was verified by periodically doing experiments with no added Ni and verifying that pentachlorophenol with higher TEQ was produced. For example, one such run with no added Ni led to a TEQ concentration at the maximum tetrachlorophenol yield of 0.79 ppm and a TEQ concentration in the final post-reaction sample of 2.4 ppm. These values are higher than those that appear for runs with added Ni.

Additional Catalyst

As catalyst concentrations greater than 0.25 wt. % appeared to have a modest effect on reducing the TEQ concentration in the pentachlorophenol product (see FIG. 3A), experiments were conducted to test the behavior of additional $AlCl_3$ catalyst (0.75 wt. % and 1.50 wt. %) when nickel was also added. In each of these experiments, the temperature ramp was terminated at 180° C., where the chlorine flow was stopped.

Figure 11A:
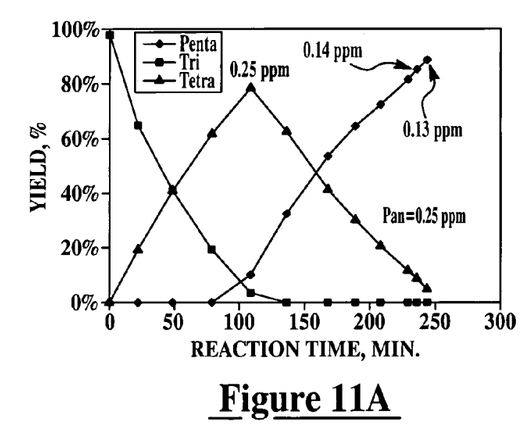
FIGS. 11A and 11B are graphs depicting temporal variation of chlorophenol yields and TEQ concentrations for synthesis with chlorine flow stopped at 180° C., 2500 ppm nickel added at 90° C., and the addition of 0.75 wt. % $AlCl_3$ and 1.5 wt. % $AlCl_3$ respectively.
Figure 11B:
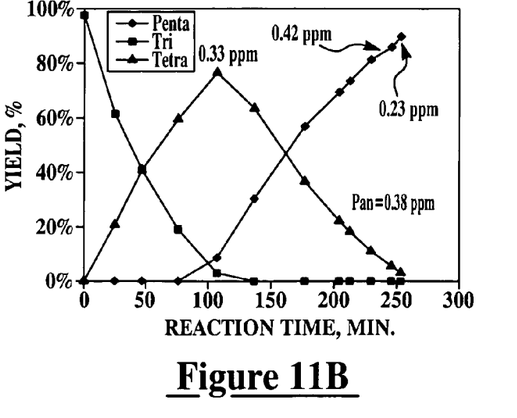

The results from a run with the 0.25 wt. % catalyst concentration appears in FIG. 10C. FIGS. 11A and 11B show the results for the experiments with 0.75 wt. % catalyst and 1.5 wt. % catalyst, respectively. In spite of the different catalyst concentrations, the final samples taken from the reactor had similar TEQ concentrations (about 0.25, about 0.13, and about 0.23 ppm for 0.25, 0.75 and 1.5 wt. % catalyst, respectively). The TEQ concentrations in the post-reaction samples taken from the aluminum pans were also similar (about 0.34, about 0.25, and about 0.38 ppm, for 0.25, 0.75 and 1.5 wt. % catalyst, respectively). The results indicate that running the synthesis at catalyst concentrations higher than 0.25 wt. % has little or no appreciable effect on the TEQ concentrations when Ni is also added to the reactor.

Varying Nickel Concentration

Figure 12A:
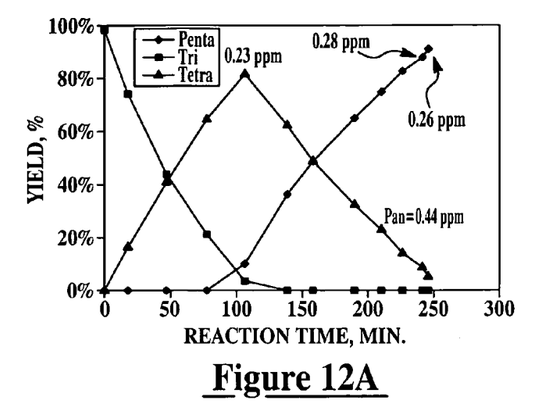
FIGS. 12A-12D are graphs depicting temporal variation of chlorophenol yields and TEQ concentrations for synthesis with chlorine flow stopped at 180° C., and, respectively, 5000 ppm, 1250 ppm, 833 ppm, and 100 ppm nickel added at 90° C.

The effects of adding more and less nickel during the pentachlorophenol synthesis were tested. FIG. 12A shows the results from a synthesis experiment with 5000 ppm nickel added. The TEQ concentrations for the last sample from the reactor and for the post-reaction sample were about 0.26 ppm and about 0.44 ppm, respectively. These values do not differ appreciably from the TEQ levels obtained with less Ni, which indicates that the higher Ni level did not appear to reduce the TEQ level any further.

Figure 12B:
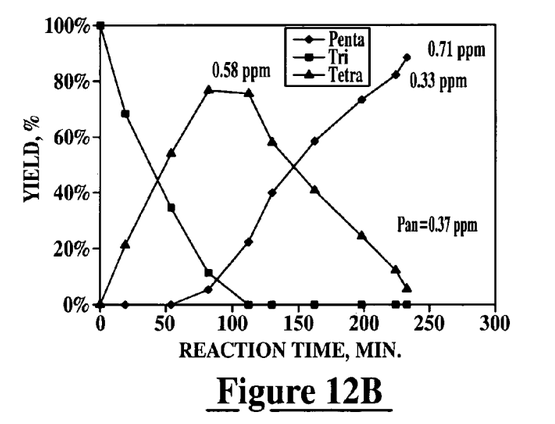

FIG. 12B shows the results from a synthesis using about 1250 ppm nickel. About 84% pentachlorophenol was produced at 225 minutes, with 12% tetrachlorophenol and about 0.33 ppm TEQ. About 90% pentachlorophenol was obtained at 234 minutes and 180° C., with 5% tetrachlorophenol residual and about 0.71 ppm TEQ. The pentachlorophenol yield in the post-reaction sample was about 89% with 5% tetrachlorophenol and about 0.37 ppm TEQ.

Figure 12C:
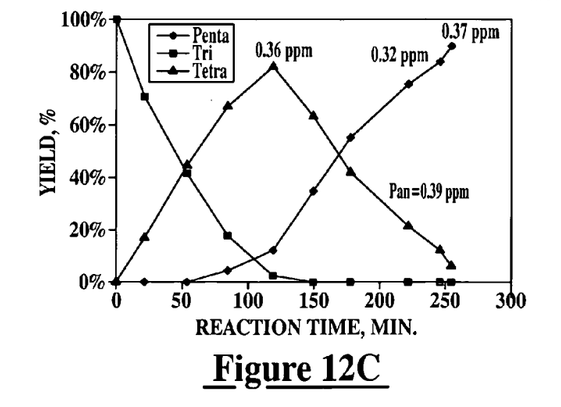

FIG. 12C shows the results from a synthesis using about 833 ppm nickel. In the last sample from the reactor (taken at 180° C. and 255 minutes), the pentachlorophenol yield was about 90%, with 7% tetrachlorophenol remaining and about 0.37 ppm TEQ concentration. The TEQ concentration in the post-reaction pentachlorophenol sample, where the pentachlorophenol yield was about 87% with 6% tetra, was about 0.39 ppm.

Figure 12D:
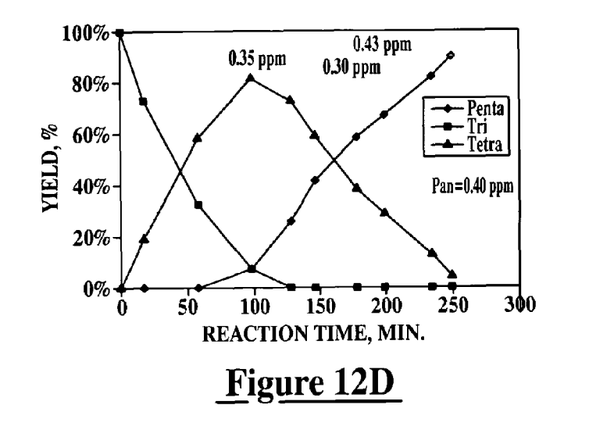

FIG. 12D shows results from a synthesis using about 100 ppm nickel. The TEQ concentrations were about 0.4 ppm. The results shown in FIGS. 12B-12D indicate that using about 100 ppm, about 833 ppm, or about 1250 ppm of nickel provides substantially similar TEQ concentrations (from about 0.3 to about 0.4 ppm) in the final pentachlorophenol product as using 2500 ppm nickel.

Synthesis Starting with Phenol

About 143 g of phenol (instead of trichlorophenol) was used in this synthesis. About 0.75 g of Ni powder was added to the reactor at 105° C. (300 minutes). A total of about 1.5 g of $AlCl_3$ was used, with 0.75 g added at 60° C. and 0.75 g added at 105° C. The same stirring rate (100-120 RPM) and chlorine flow rate (1.5 mol/hr) used in experiments that started with trichlorophenol were used in this experiment. Samples were collected about every 30 min. The reaction required about 10 hours to reach to a desired end point. The chlorine flow and temperature ramp were terminated at about 180° C., so that some tetrachlorophenol remained in the final product.

The chlorinated phenols that formed were 2-, and 4-chlorophenol, 2,4- and 2,6-dichlorophenol, 2,4,6-trichlorophenol, tetrachlorophenol, and pentachlorophenol. The yields were analyzed by gas chromatography with thermal conductivity detection. The chlorophenol yields, TEQ concentrations, and the reactor temperature (illustrated by the Δ plot line) are depicted in FIG. 13.

The yields of the two mono- and two dichlorophenols were summed in the plot. The mono-, di-, and trichlorophenol yields increased to maximum values of about 87% at 60 minutes, about 81% at 121 minutes, and about 92% at 246 minutes, respectively, and then decreased to zero at the time the next product reached its maximum yield (i.e., the monochlorophenol yield was zero at the time the dichlorophenol yield was at its maximum). The yield of tetrachlorophenol increased to its maximum of about 79% at 434 minutes. About 12% tetrachlorophenol remained at 589 minutes, where the pentachlorophenol yield was about 79%. The TEQ concentrations were about 0.14, about 0.11, and about 0.13 ppm, for the samples with the maximum mono-, di-, and trichlorophenol yields. These quantitative results should be viewed as estimates, because the chemical matrix in these samples differed from that in the more highly chlorinated pentachlorophenol standards used to calibrate the bioassay. Nevertheless, the results indicate that the TEQ concentrations are very low (~0.1 ppm) until tetrachlorophenol was formed. The TEQ concentration increased to about 0.43 ppm at the maximum tetrachlorophenol yield. It subsequently increased further to about 0.79 ppm and about 1.10 ppm for the last pentachlorophenol sample from the reactor and the post-reaction pentachlorophenol sample, respectively.

Figure 13:
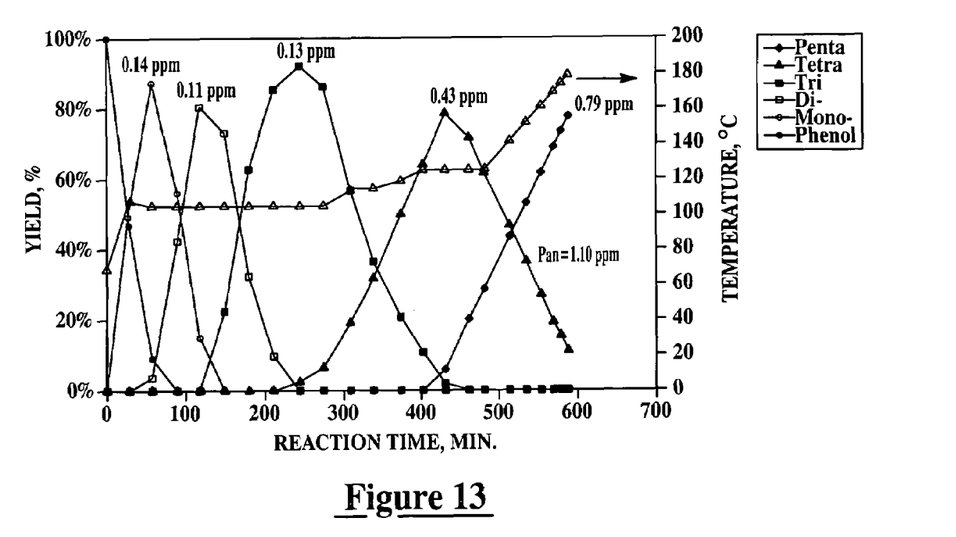
FIG. 13 is a graph depicting temporal variation of chlorophenol yields and TEQ concentrations for synthesis starting with phenol, with chlorine flow and temperature ramp stopped at 180° C., and 2500 ppm Ni added at 90° C.

The results in FIG. 13 may be compared with results from a similar phenol chlorination experiment without added Ni (see FIG. 8). The previous experiments without added Ni led to a TEQ concentration near the end of the run of about 1.9±0.5 ppm. The end-of-run TEQ concentrations in FIG. 13 are only about half as large. This result again exhibits that adding Ni reduces the TEQ concentration in the pentachlorophenol product, in this instance for chlorination starting with phenol.

Effect of Other Metals

Since it had been demonstrated that Ni powder has an effect on the TEQ concentration in pentachlorophenol, other metals were tested for similar effects. Pentachlorophenol was synthesized in the presence of the $AlCl_3$ catalyst and about 2500 ppm of other transition metals (including Mn, Co, Mo, W, V, Ti, Cu, Fe, and Zn). These metals were added to the reactor as powders along with the $AlCl_3$ catalyst.

The temporal variation of the yields of chlorophenols were nearly identical in these experiments. One noticeable difference was for the synthesis in the presence of Cu. This reaction took longer than the other experiments with added metal. The results indicated that that copper inhibits the chlorination reaction.

Table 1 summarizes the results for TEQ analyses from samples taken at comparable reaction points with the different added metals. The first row shows the mean values (±std. dev.) from experiments in which the chlorine flow was terminated between 177° C. and 183° C., and no Ni was added. The second row shows the mean values (±std. dev.) for all runs with Ni added at the start of the reaction. The remaining rows show results from single analyses of single samples from an individual experimental run. The data in the first two rows illustrates that adding Ni reduces the TEQ concentration in the post-reaction sample by about one third. The TEQ concentrations in row 2, with added Ni, are all about the same, whereas the TEQ concentrations in row 1, without added Ni appear to increase during the reaction. Thus, it appears that Ni inhibits the formation of toxic microcontaminants that would otherwise form after the maximum tetrachlorophenol yield has been reached.

TABLE 1

TEQ Concentrations (ppm) from Synthesis in the Presence of Metal Powders

| Metal | Sample | | | |
|---|---|---|---|---|
| | Maximum Tetrachlorophenol Yield | Next to Last Reactor Sample | Final Reactor Sample | Post-Reaction Sample |
| None | 0.38 ± 0.12 | | 0.53 ± 0.14 | 0.59 ± 0.18 |
| Ni (mean) | 0.38 ± 0.14 | 0.32 ± 0.13 | 0.39 ± 0.16 | 0.42 ± 0.11 |
| Ni (FIG. 9C) | 0.34 | 0.33 | 0.29 | 0.34 |
| Ni (FIG. 10A) | 0.39 | 0.07 | 0.53 | 0.46 |
| Ni (FIG. 10B) | 0.37 | 0.38 | 0.50 | 0.65 |
| Ni (FIG. 10C) | 0.28 | 0.51 | 0.25 | 0.34 |
| Ni (FIG. 11A) | 0.25 | 0.14 | 0.13 | 0.25 |
| Ni (FIG. 11B) | 0.33 | 0.42 | 0.23 | 0.38 |
| Ni (FIG. 12A) | 0.23 | 0.28 | 0.26 | 0.44 |
| Ni (FIG. 12B) | 0.58 | 0.33 | 0.71 | 0.37 |
| Ni (FIG. 12C) | 0.36 | 0.32 | 0.37 | 0.39 |
| Ni (FIG. 12D) | 0.35 | 0.30 | 0.43 | 0.40 |
| Mn | 0.33 | 0.34 | 0.35 | 0.57 |
| Co | 0.18 | 0.25 | 0.29 | 0.35 |
| Mo | 0.40 | 0.20 | 0.64 | 0.42 |
| W | 0.31 | 0.24 | 0.55 | 0.90 |
| V | 0.74 | 0.45 | 0.69 | 0.84 |
| Ti | 0.49 | 0.60 | 0.62 | 1.13 |
| Cu | 1.01 | 0.67 | 0.88 | 0.79 |
| Fe | 0.34 | 0.51 | 0.90 | 0.93 |
| Zn | 0.15 | 0.43 | 0.46 | 0.80 |

In the experiments with added metal, the TEQ concentrations were below about 1 ppm in all but two sample. Some of the metals tested appear to be modestly more effective at lowering TEQ than others. If one lists the four metals that gave the lowest TEQ values for the last sample withdrawn from the reactor and the four metals that gave the lowest TEQ values for the sample taken from the post-reaction solidified product, Ni, Co, and Mn appear on both lists. The mean TEQ concentration in these samples for these three metals was about 0.39 ppm. Likewise, if one lists the four metals that gave the highest TEQ concentrations for both samples, Fe and V are appear on both lists. The mean TEQ concentration for these samples with these two metals was about 0.84 ppm.

Embodiments of the method disclosed herein advantageously reduce the amount of microcontaminants formed during the synthesis of pentachlorophenol.

While several embodiments have been described in detail, it will be apparent to those skilled in the art that the disclosed embodiments may be modified. Therefore, the foregoing description is to be considered exemplary rather than limiting.

What is claimed is:

1. A method for reducing microcontaminants during synthesis of pentachlorophenol, comprising:
    providing a phenol-based starting material and a catalyst, the phenol-based starting material and catalyst forming a reaction mixture;
    introducing a chlorine flow in contact with the reaction mixture, and reacting the starting material and the chlorine via a temperature-programmed reaction;
    terminating the chlorine flow at a predetermined temperature prior to an end of the temperature-programmed reaction; and
    continuing the temperature-programmed reaction for a time period of at least about 5 minutes after terminating the chlorine flow.

2. The method as defined in claim 1 wherein the chlorine flow is introduced at a first flow rate, and the method further includes:
    reducing the first flow rate to a second flow rate after a first predetermined time period lapses; and
    reducing the second flow rate to a third flow rate after a second predetermined time period lapses.

3. The method as defined in claim 1 wherein the phenol-based starting material is selected from chlorophenols, phenols, and combinations thereof.

4. The method as defined in claim 3 wherein the phenol-based starting material is 2,4,6-trichlorophenol, and wherein a toxic equivalent concentration of contaminants in a post-reaction sample of pentachlorophenol is less than about 0.85 ppm.

5. The method as defined in claim 3 wherein the phenol-based starting material is phenol, and wherein a toxic equivalent concentration of contaminants in a post-reaction sample of pentachlorophenol is less than about 2.4 ppm.

6. The method as defined in claim 1, further comprising adding to the reaction mixture a material selected from nickel, cobalt, manganese, and combinations thereof prior to terminating the chlorine flow.

7. The method as defined in claim 6 wherein the material is added so that its concentration in the reaction mixture is at least about 100 ppm.

8. The method as defined in claim 6 wherein the material is added so that its concentration in the reaction mixture is from about 800 ppm to about 5000 ppm.

9. The method as defined in claim 6 wherein the phenol-based starting material is 2,4,6-trichlorophenol, and wherein a toxic equivalent concentration of contaminants in a post-reaction sample of pentachlorophenol is less than about 0.5 ppm.

10. The method as defined in claim 6 wherein the material is nickel, the phenol-based starting material is phenol, and wherein a toxic equivalent concentration of contaminants in a post-reaction sample of pentachlorophenol is not greater than about 1.1 ppm.

11. The method as defined in claim 1 wherein at least the chlorine flow introducing step is carried out substantially in a liquid phase.

12. The method as defined in claim 1 wherein the predetermined temperature at which the chlorine flow is terminated ranges from about 170° C. to about 190° C.

13. The method as defined in claim 1, further comprising purging the reaction mixture with nitrogen after terminating the chlorine flow.

14. The method as defined in claim 1, further comprising adding one of an aluminum catalyst and tetrachlorophenol to the reaction mixture after terminating the chlorine flow.

15. A method for synthesizing pentachlorophenol, comprising:
reacting a phenol-based starting material and a catalyst via a temperature-programmed reaction, the phenol-based starting material and catalyst forming a reaction mixture;
introducing a chlorine flow in contact with the reaction material;
terminating the chlorine flow at a point where the yield of pentachlorophenol based on the amount of starting material is less than about 95%; and
continuing the temperature-programmed reaction for a time period of at least about 5 minutes after terminating the chlorine flow.

16. The method as defined in claim 15 wherein the phenol-based starting material is selected from chlorophenols, phenols, and combinations thereof.

17. The method as defined in claim 15 wherein the phenol-based starting material is 2,4,6-trichlorophenol, and wherein a toxic equivalent concentration of contaminants in a post-reaction sample of pentachlorophenol is less than about 0.85 ppm.

18. The method as defined in claim 15 wherein the phenol-based starting material is phenol, and wherein a toxic equivalent concentration of contaminants in a post-reaction sample of pentachlorophenol is less than about 2.4 ppm.

19. The method as defined in claim 15, further comprising adding to the reaction mixture a material selected from nickel, cobalt, manganese, and combinations thereof prior to terminating the chlorine flow.

20. The method as defined in claim 19 wherein the material is added so that its concentration in the reaction mixture is from about 100 ppm to about 5000 ppm.

21. The method as defined in claim 19 wherein the phenol-based starting material is 2,4,6-trichlorophenol, and wherein a toxic equivalent concentration of contaminants in a post-reaction sample of pentachlorophenol is less than about 0.5 ppm.

22. The method as defined in claim 19 wherein the material is nickel, the phenol-based starting material is phenol, and wherein a toxic equivalent concentration of contaminants in a post-reaction sample of pentachlorophenol is not greater than about 1.1 ppm.

23. The method as defined in claim 15 wherein at least the chlorine flow introducing step is carried out substantially in a liquid phase.

24. The method as defined in claim 15 wherein the predetermined temperature at which the chlorine flow is terminated ranges from about 170° C. to about 190° C.

25. The method as defined in claim 15 wherein the chlorine flow terminating step is carried out at a point where the yield of tetrachlorophenol remains greater than about 2%.

26. The method as defined in claim 15 wherein the chlorine flow terminating step is carried out at a point where the yield of pentachlorophenol is less than about 85%.

27. The method as defined in claim 15 wherein the chlorine flow terminating step is carried out at a point where the yield of pentachlorophenol is less than about 80%.

* * * * *